(12) United States Patent
Okazaki et al.

(10) Patent No.: US 10,292,684 B2
(45) Date of Patent: May 21, 2019

(54) ULTRASOUND DIAGNOSIS APPARATUS AND IMAGE PROCESSING METHOD

(71) Applicant: Toshiba Medical Systems Corporation, Otawara-shi (JP)

(72) Inventors: Tomoya Okazaki, Kawasaki (JP); Yasuhiko Abe, Otawara (JP); Koji Ando, Otawara (JP); Shogo Fukuda, Kawasaki (JP); Yurika Ogawa, Yokohama (JP); Yukinobu Sakata, Kawasaki (JP); Yasunori Taguchi, Kawasaki (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 23 days.

(21) Appl. No.: 15/442,000

(22) Filed: Feb. 24, 2017

(65) Prior Publication Data
US 2017/0245835 A1    Aug. 31, 2017

(30) Foreign Application Priority Data

Feb. 26, 2016 (JP) .................................. 2016-036354
Feb. 23, 2017 (JP) .................................. 2017-032564

(51) Int. Cl.
*G06K 9/00* (2006.01)
*A61B 8/08* (2006.01)
(Continued)

(52) U.S. Cl.
CPC .............. *A61B 8/5223* (2013.01); *A61B 6/12* (2013.01); *A61B 8/0841* (2013.01);
(Continued)

(58) Field of Classification Search
None
See application file for complete search history.

(56) References Cited

U.S. PATENT DOCUMENTS

| 5,797,849 A * | 8/1998 | Vesely | ............... A61B 5/0422 600/461 |
| 7,697,972 B2 * | 4/2010 | Verard | ............... A61B 1/00071 600/407 |

(Continued)

FOREIGN PATENT DOCUMENTS

JP    4205957    1/2009

*Primary Examiner* — Shervin K Nakhjavan
(74) *Attorney, Agent, or Firm* — Oblon, McClelland, Maier & Neustadt, L.L.P.

(57) ABSTRACT

An ultrasound diagnosis apparatus includes processing circuitry. The processing circuitry obtains three-dimensional medical image data, taken by using an ultrasound probe, of a region including a heart valve of a patient and a catheter inserted into a heart chamber of the patient. The processing circuitry determines an advancing direction of a tip end part of the catheter by obtaining information on a position and a posture of the tip end part included in the three-dimensional medical image data, by using at least one selected from shape information indicating the shape of the tip end part and reflection characteristic information indicating ultrasound reflection characteristics of the tip end part. The processing circuitry generates a display image from the three-dimensional medical image data in accordance with the position and the advancing direction of the tip end part. The processing circuitry causes the display image to be displayed.

19 Claims, 10 Drawing Sheets

(51) Int. Cl.
*G06T 7/00* (2017.01)
*G06T 7/70* (2017.01)
*G06T 7/20* (2017.01)
*A61B 8/00* (2006.01)
*A61M 25/01* (2006.01)
*A61B 6/12* (2006.01)
*A61B 34/20* (2016.01)
*A61F 2/24* (2006.01)

(52) U.S. Cl.
CPC ............ *A61B 8/0883* (2013.01); *A61B 8/463* (2013.01); *A61B 8/466* (2013.01); *A61B 8/483* (2013.01); *A61B 8/5261* (2013.01); *A61M 25/0108* (2013.01); *G06T 7/0012* (2013.01); *G06T 7/20* (2013.01); *G06T 7/70* (2017.01); *A61B 2034/2063* (2016.02); *A61B 2034/2065* (2016.02); *A61F 2/2466* (2013.01); *G06T 2207/10136* (2013.01); *G06T 2207/30048* (2013.01)

(56) References Cited

U.S. PATENT DOCUMENTS

| | | | | |
|---|---|---|---|---|
| 2003/0074011 | A1* | 4/2003 | Gilboa | A61B 5/06 606/130 |
| 2005/0256398 | A1* | 11/2005 | Hastings | A61B 34/73 600/423 |
| 2006/0058647 | A1* | 3/2006 | Strommer | A61B 5/06 600/434 |
| 2007/0167801 | A1* | 7/2007 | Webler | G06T 19/00 600/459 |
| 2008/0146942 | A1* | 6/2008 | Dala-Krishna | A61B 6/12 600/466 |
| 2009/0143677 | A1* | 6/2009 | Govari | A61B 8/0883 600/439 |
| 2010/0016709 | A1* | 1/2010 | Gilboa | A61B 5/06 600/424 |
| 2017/0301124 | A1* | 10/2017 | Dala-Krishna | G06T 13/20 |

* cited by examiner

ULTRASOUND DIAGNOSIS APPARATUS AND IMAGE PROCESSING METHOD

CROSS-REFERENCE TO RELATED APPLICATIONS

This application is based upon and claims the benefit of priority from Japanese Patent Application No. 2016-36354, filed on Feb. 26, 2016; and Japanese Patent Application No. 2017-032564, filed on Feb. 23, 2017, the entire contents of all of which are incorporated herein by reference.

FIELD

Embodiments described herein relate generally to an ultrasound diagnosis apparatus and an image processing method.

BACKGROUND

Conventionally, various types of techniques have been proposed by which a heart surgery treatment is aided by taking an image of the inside of the body of the examined subject (hereinafter, "patient"). For example, among various treatments of mitral valve closing insufficiency is a treatment by which the volume of regurgitation is reduced by inserting a catheter to the mitral valve of the heart through a blood vessel in a thigh (a femoral vein) and holding the mitral valve with a clip-shaped tool. For such a treatment, for example, a technique has been proposed by which the position of the tool (the catheter) inserted toward the mitral valve is accurately displayed by using an X-ray fluoroscopic image and a Transesophageal Echocardiography (TEE) image taken during the surgical operation. Further, for example, another technique has also been proposed by which an image for guiding an advancing course of the catheter is displayed by aligning the position of a Computed Tomography (CT) image taken prior to the surgical operation with the position of an image taken during the surgical operation.

Further, techniques have been proposed by which the field of vision is varied so as to follow movements of a puncture needle.

DETAILED DESCRIPTION

An ultrasound diagnosis apparatus according to an embodiment includes processing circuitry. The processing circuitry is configured to obtain three-dimensional medical image data, taken by using an ultrasound probe, of a region including a heart valve of a patient and a catheter inserted into a heart chamber of the patient. The processing circuitry is configured to determine an advancing direction of a tip end part of the catheter by obtaining information on a position and a posture of the tip end part included in the three-dimensional medical image data, by using at least one selected from shape information indicating the shape of the tip end part and reflection characteristic information indicating ultrasound reflection characteristics of the tip end part. The processing circuitry is configured to generate a display image from the three-dimensional medical image data in accordance with the position and the advancing direction of the tip end part. The processing circuitry is configured to cause the display image to be displayed.

Exemplary embodiments of an ultrasound diagnosis apparatus and an image processing method will be explained below, with reference to the accompanying drawings.

First Embodiment

Figure 1:
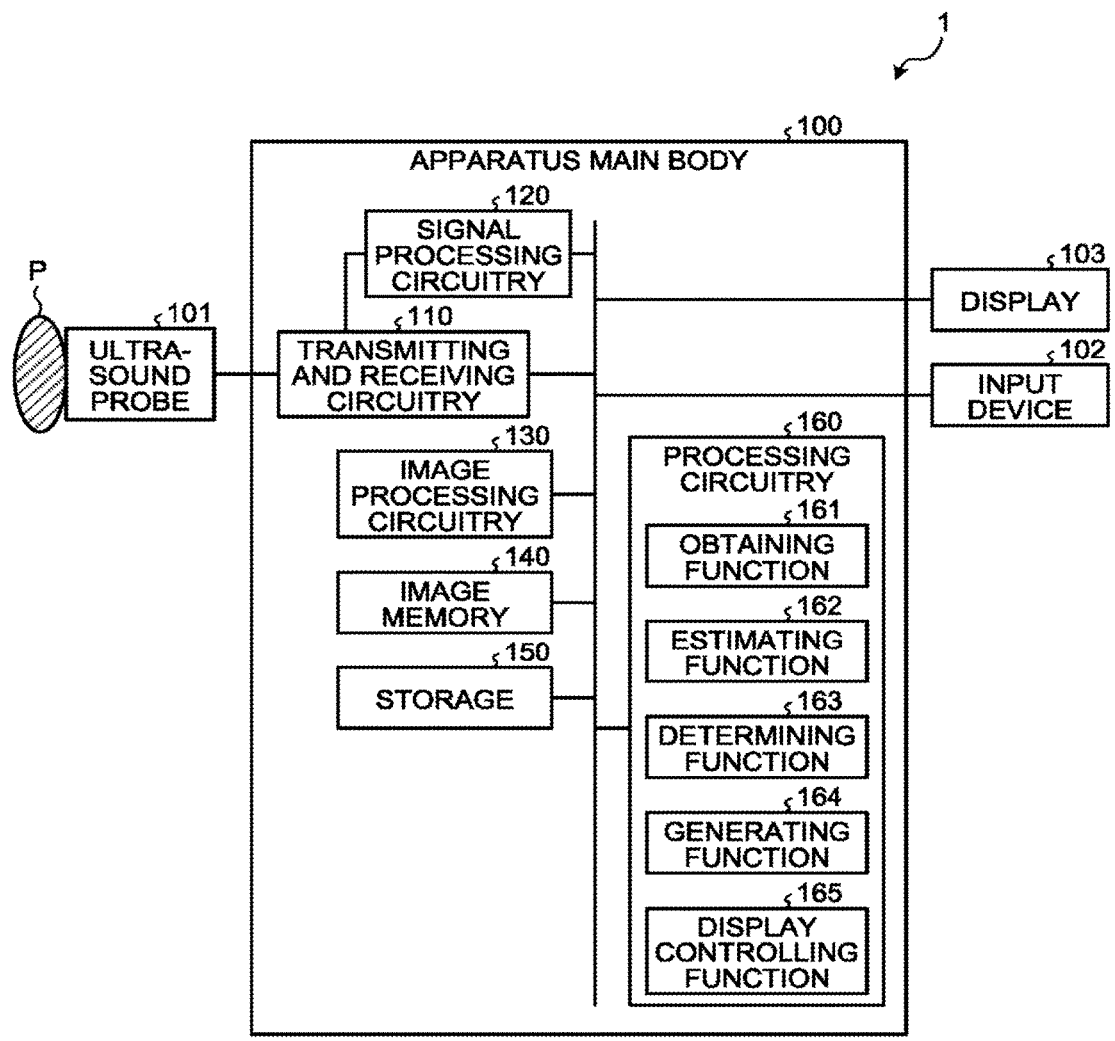
FIG. 1 is a diagram illustrating an ultrasound diagnosis apparatus according to a first embodiment.

FIG. 1 is a diagram illustrating an example of an ultrasound diagnosis apparatus 1 according to a first embodiment. As illustrated in FIG. 1, the ultrasound diagnosis apparatus 1 according to the first embodiment includes an ultrasound probe 101, an input device 102, a display 103, and an apparatus main body 100. The ultrasound probe 101, the input device 102, and the display 103 are connected so as to be able to communicate with the apparatus main body 100. The examined subject (hereinafter, "patient") P is not included in the configuration of the ultrasound diagnosis apparatus 1.

The ultrasound probe 101 is configured to transmit and receive an ultrasound wave. For example, the ultrasound probe 101 includes a plurality of piezoelectric transducer elements (not illustrated). The plurality of piezoelectric transducer elements are configured to generate an ultrasound wave on the basis of a drive signal supplied thereto from transmitting and receiving circuitry 110 included in the apparatus main body 100 (explained later). Further, the plurality of piezoelectric transducer elements included in the ultrasound probe 101 are configured to receive reflected waves from the patient P and convert the received reflected waves into electrical signals. Further, the ultrasound probe 101 includes matching layers (not illustrated) provided for the piezoelectric transducer elements, as well as a backing member (not illustrated) or the like that prevents ultrasound waves from propagating rearward from the piezoelectric transducer elements. In this situation, the ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P. The reflected wave is received as a reflected-wave signal by each of the plurality of piezoelectric transducer elements included in the ultrasound probe 101. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

For example, the ultrasound probe 101 according to the first embodiment may be a Transesophageal Echocardiography (TEE) probe. The ultrasound probe 101 serving as a TEE probe is inserted into the body of the patient P through the mouth of the patient P and is arranged to abut against an upper digestive tract such as the esophagus, the stomach, or the like. Further, by mechanically causing the plurality of piezoelectric transducer elements to rotate, the ultrasound probe 101 is configured to image an arbitrary cross-sectional plane or to acquire three-dimensional ultrasound image data (volume data). Alternatively, the ultrasound probe 101 may be a two-dimensional array ultrasound probe in which a plurality of ultrasound transducer elements are arranged in a matrix formation so as to be able to perform a three-dimensional ultrasound scan on the patient P. The two-dimensional array ultrasound probe is capable of three-dimensionally scan the patient P electronically, by transmitting and receiving ultrasound waves in an electronically-converged manner. In this situation, three-dimensional ultrasound image data is an example of three-dimensional medical image data.

The input device 102 corresponds to one or more devices such as a mouse, a keyboard, a button, a panel switch, a touch command screen, a foot switch, a trackball, and/or a joystick. The input device 102 is configured to receive various types of setting requests from an operator of the ultrasound diagnosis apparatus 1 and to transmit the received various types of setting requests to the apparatus main body 100.

The display 103 is configured to display a Graphical User Interface (GUI) used by the operator of the ultrasound diagnosis apparatus 1 to input the various types of setting requests through the input device 102 and to display ultrasound image data generated by the apparatus main body 100 or the like.

The apparatus main body 100 is configured to generate the ultrasound image data on the basis of the reflected-wave signals received by the ultrasound probe 101. The ultrasound image data generated by the apparatus main body 100 may be two-dimensional ultrasound image data generated on the basis of two-dimensional reflected-wave signals or may be three-dimensional ultrasound image data generated on the basis of three-dimensional reflected-wave signals.

As illustrated in FIG. 1, the apparatus main body 100 includes the transmitting and receiving circuitry 110, signal processing circuitry 120, image processing circuitry 130, an image memory 140, a storage 150, and processing circuitry 160. The transmitting and receiving circuitry 110, the signal processing circuitry 120, the image processing circuitry 130, the image memory 140, the storage 150, and the processing circuitry 160 are connected to one another so as to be able to communicate with one another.

The transmitting and receiving circuitry 110 is configured to control ultrasound transmissions and receptions performed by the ultrasound probe 101, on the basis of an instruction from the processing circuitry 160 (explained later). The transmitting and receiving circuitry 110 includes a pulse generator (not illustrated), a transmission delay circuit (not illustrated), a pulser (not illustrated), and the like and is configured to supply the drive signal to the ultrasound probe 101. The pulse generator is configured to repeatedly generate a rate pulse used for forming a transmission ultrasound wave, at a predetermined repetition frequency called a Pulse Repetition Frequency (PRF). Further, the transmission delay circuit is configured to apply a delay period that is required to converge the ultrasound wave generated by the ultrasound probe 101 into the form of a beam and to determine transmission directionality and that corresponds to each of the piezoelectric transducer elements, to each of the rate pulses generated by the pulse generator. Further, the pulser is configured to apply the drive signal (a drive pulse) to the ultrasound probe 101 with timing based on the rate pulses. In other words, by varying the delay periods applied to the rate pulses, the transmission delay circuit is able to arbitrarily adjust the transmission directions of the ultrasound waves transmitted from the surfaces of the piezoelectric transducer elements.

In this situation, the transmitting and receiving circuitry 110 is able to instantly change the transmission frequency, the transmission drive voltage, and the like, for the purpose of executing a predetermined scanning sequence on the basis of an instruction from the processing circuitry 160 (explained later). In particular, the configuration to change the transmission drive voltage is realized by using a linear-amplifier-type transmission circuit (not illustrated) of which the value can be instantly switched or by using a mechanism configured to electrically switch between a plurality of power source units (not illustrated).

Further, for example, the transmitting and receiving circuitry 110 includes an amplifying circuit (not illustrated) an analog/digital (A/D) converter (not illustrated), an adder (not illustrated), and a phase detecting circuit (not illustrated) and is configured to generate the reflected-wave data by performing various types of processing processes on the reflected-wave signals received by the ultrasound probe 101. The amplifying circuit is configured to perform a gain correcting process by amplifying the reflected-wave signal for each of the channels. The A/D converter is configured to apply an A/D conversion to the gain-corrected reflected-wave signals and to apply a delay period required to determine reception directionality, to the digital data. The adder is configured to perform an adding process on the reflected-wave signals processed by the A/D converter. As a result of the adding process performed by the adder, reflected components from the direction corresponding to the reception directionality of the reflected-wave signals are emphasized. The phase detecting circuit is configured to convert an output signal from the adder into an In-phase signal (which may be referred to as an "I signal") and a Quadrature-phase signal (which may be referred to as a "Q signal") in a baseband. Further, the phase detecting circuit forwards the I signal and the Q signal (the IQ signals) to the signal processing circuitry 120 at a following stage. The data prior to the process performed by the phase detecting circuit may be referred to as an RF signal. In the following explanation, "the IQ signals and the RF signal" generated on the basis of the reflected waves of the ultrasound waves will collectively referred to as "reflected-wave data".

The signal processing circuitry 120 is configured to perform various types of signal processing processes on the reflected-wave data generated from the reflected-wave signals by the transmitting and receiving circuitry 110. The signal processing circuitry 120 generates data (B-mode data) in which signal intensities at multiple points are expressed by degrees of brightness, by performing a logarithmic amplification, an envelope detection process, a logarithmic compression, and/or the like on the reflected-wave data (the IQ signals) read from a buffer.

Further, the signal processing circuitry 120 is configured to generate data (Doppler data) obtained by extracting motion information based on a Doppler effect exerted on mobile members within a scanned range, by performing a frequency analysis on the reflected-wave data. More specifically, as the motion information of the mobile members, the signal processing circuitry 120 generates the Doppler data obtained by estimating an average velocity value, an average dispersion value, an average power value, and the like at each of multiple sampling points. In this situation, examples of the mobile members include a blood flow, tissues such as the cardiac wall, and a contrast agent. As the motion information of a blood flow (blood flow information), the signal processing circuitry 120 according to the present embodiment generates Doppler data obtained by estimating, at each of the multiple sampling points, an average velocity value of the blood flow, an average dispersion value of the blood flow, an average power value of the blood flow, and/or the like.

The image processing circuitry 130 is configured to generate the ultrasound image data from the various types of data generated by the signal processing circuitry 120. The image processing circuitry 130 generates two-dimensional B-mode image data expressing intensities of the reflected waves by using brightness levels, from two-dimensional B-mode data generated by the signal processing circuitry 120. Further, the image processing circuitry 130 generates two-dimensional Doppler image data expressing the blood flow information in a picture, from the two-dimensional Doppler data generated by the signal processing circuitry 120. The two-dimensional Doppler image data is velocity image data, dispersion image data, power image data, or image data combining any of these. As the Doppler image data, the image processing circuitry 130 generates color Doppler image data in which the blood flow information is displayed in color and/or generates Doppler image data in which one piece of blood flow information is displayed by using a gray scale. The image processing circuitry 130 is an example of an image generating unit.

In this situation, generally speaking, the image processing circuitry 130 converts (by performing a scan convert process) a scanning line signal sequence from an ultrasound scan into a scanning line signal sequence in a video format used by, for example, television and generates the ultrasound image data. More specifically, the image processing circuitry 130 generates the ultrasound image data by performing a coordinate transformation process compliant with the ultrasound scanning mode used by the ultrasound probe 101. Further, besides the scan convert process, the image processing circuitry 130 may perform various types of image processing processes. For example, the image processing circuitry 130 may perform an image processing process (a smoothing process) to re-generate an average-brightness-value image or an image processing process (an edge enhancement process) that employs a differential filter within the image, by using a plurality of image frames that are available after the scan convert process. Further, the image processing circuitry 130 combines text information of various parameters, scale graduations, body marks, and the like with the ultrasound image data.

In other words, the B-mode data and the Doppler data are each ultrasound image data before the scan covert process, whereas the data generated by the image processing circuitry 130 is the ultrasound image data after the scan covert process. The B-mode data and the Doppler data may each be referred to as "raw data". The image processing circuitry 130 generates two-dimensional ultrasound image data from the two-dimensional ultrasound image data before the scan convert process.

Further, the image processing circuitry 130 generates three-dimensional B-mode image data by performing a coordinate transformation process on three-dimensional B-mode data generated by the signal processing circuitry 120. Further, the image processing circuitry 130 generates three-dimensional Doppler image data by performing a coordinate transformation process on three-dimensional Doppler data generated by the signal processing circuitry 120.

Further, the image processing circuitry 130 performs rendering processes on the volume data, for the purpose of generating various types of two-dimensional image data used for displaying the volume data on the display 103. Examples of the rendering processes performed by the image processing circuitry 130 include a process to generate Multi Planar Reconstruction (MPR) image data from the volume data by implementing an MPR method. Another example of the rendering processes performed by the image processing circuitry 130 is a Volume Rendering (VR) process to generate two-dimensional image data reflecting three-dimensional information.

The image memory 140 is a memory configured to store therein the ultrasound image data generated by the image processing circuitry 130. Further, the image memory 140 is also capable of storing therein data generated by the signal processing circuitry 120. After a diagnosis process, for example, the operator is able to invoke the B-mode data and the Doppler data stored in the image memory 140. The invoked data serves as ultrasound image data after being routed through the image processing circuitry 130. Also, the image memory 140 is also capable of storing therein the reflected-wave data output by the transmitting and receiving circuitry 110.

The storage 150 is configured to store therein control computer programs to realize the ultrasound transmissions and receptions, image processing, and display processing, as well as various types of data such as diagnosis information (e.g., patients' IDs, medical doctors' observations), diagnosis protocols, and various types of body marks. Further, the storage 150 may be used, as necessary, for storing therein any of the image data stored in the image memory 140. Further, it is possible to transmit the data stored in the storage 150 to an external apparatus via an interface (not illustrated). Furthermore, the storage 150 is also capable of storing therein data transmitted thereto from an external apparatus via an interface (not illustrated).

The processing circuitry 160 is configured to control the overall processes performed by the ultrasound diagnosis apparatus 1. More specifically, on the basis of the various types of setting requests input by the operator via the input device 102 and the various types of control computer programs and the various types of data read from the storage 150, the processing circuitry 160 controls processes performed by the transmitting and receiving circuitry 110, the signal processing circuitry 120, and the image processing circuitry 130.

Further, the processing circuitry 160 exercises control so that the ultrasound image data stored in the image memory 140 and the storage 150 is displayed by the display 103 as a display-purpose ultrasound image. For example, the processing circuitry 160 causes the display 103 to display the color Doppler image data generated by the image processing circuitry 130 as a display-purpose color Doppler image. Further, for example, the processing circuitry 160 causes the display 103 to display the B-mode data generated by the image processing circuitry 130 as a display-purpose B-mode image.

The processing circuitry 160 executes an obtaining function 161, an estimating function 162, a determining function 163, a generating function 164, and a display controlling function 165. Processing functions executed by the obtaining function 161, the estimating function 162, the determining function 163, the generating function 164, and the display controlling function 165 are, for example, recorded in the storage 150 in the form of computer-executable programs. The processing circuitry 160 is a processor configured to realize the functions corresponding to the programs by reading and executing the programs from the storage 150. The processing circuitry 160 that has read the programs from the storage 150 has the functions illustrated within the processing circuitry 160 in FIG. 1. The processes executed by the obtaining function 161, the estimating function 162, the determining function 163, the generating function 164, and the display controlling function 165 will be explained later.

Further, in the first embodiment, an example is explained in which the single processing circuit (i.e., the processing circuitry 160) realizes the processing functions described above; however, it is also acceptable to structure a processing circuit by combining together a plurality of independent processors, so that the processors realize the functions by executing the programs.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processor realizes the functions by reading and executing the programs stored in the storage. It is also acceptable to directly incorporate the programs into the circuit of the processor, instead of storing the programs in the storage 150. In that situation, the processor realizes the functions by reading and executing the programs incorporated in the circuit thereof. Further, as for the processors according to the first embodiment, each of the processors does not necessarily have to be structured as a single circuit; it is also acceptable to structure a single processor by combining a plurality of independent circuits together so as to realize the functions thereof. Further, it is also acceptable to integrate two or more of the constituent elements illustrated in the drawings into a single processor so as to realize the functions thereof.

In the following sections, an example will be explained in which the ultrasound diagnosis apparatus 1 according to the first embodiment is used in a catheter treatment for mitral valve closing insufficiency. More specifically, the example will be explained in which the ultrasound diagnosis apparatus 1 is used for a treatment to reduce the volume of regurgitation by holding the mitral valve partitioning between the left atrium and the left ventricle of the heart while using a clip-like tool inserted by a catheter. However, possible embodiments are not limited to this example. For instance, the ultrasound diagnosis apparatus 1 is also applicable to a treatment of any other arbitrary heart valve such as the aortic valve partitioning between the left ventricle and the aorta, the tricuspid valve partitioning between the right atrium and the right ventricle, or the pulmonary valve partitioning between the right ventricle and the pulmonary artery.

The storage 150 is configured to store therein information about the catheter. For example, the storage 150 stores therein shape information indicating the shape of the tip end of the catheter and reflection characteristic information indicating ultrasound reflection characteristics of the tip end of the catheter. In other words, the storage 150 stores therein factor information indicating factors related to how the catheter is rendered in the volume data represented by the ultrasound image data. In this situation, the storage 150 is an example of a storage unit. Further, the catheter is an example of a tool.

Figure 2:
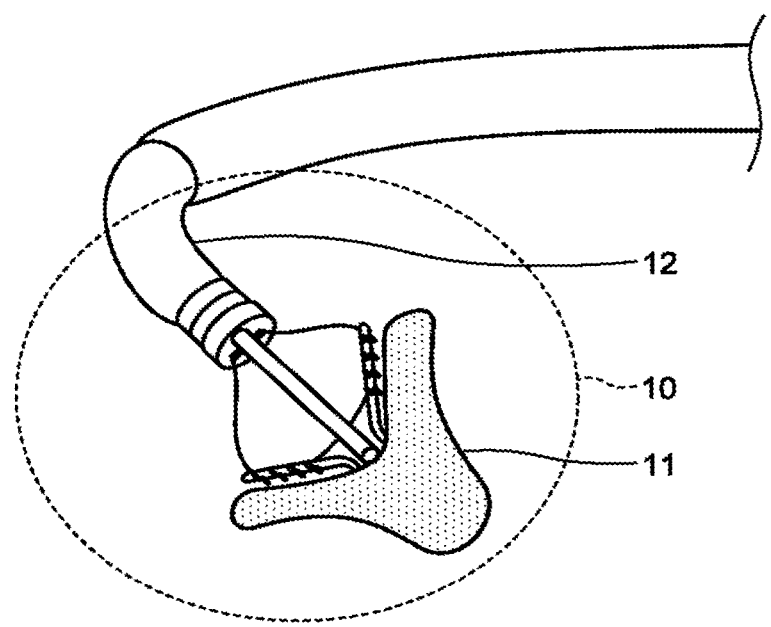
FIG. 2 is a drawing for explaining an example of information stored in a storage according to the first embodiment.

FIG. 2 is a drawing for explaining an example of the information stored in the storage 150. For example, the storage 150 stores therein information about a tip end part 10 of the catheter. In this situation, the tip end part 10 of the catheter includes, for example, a clip part 11 and a tubular part 12. The clip part 11 is a part used for holding the mitral valve. More specifically, the clip part 11 improves closing insufficiency of the mitral valve by drawing together the two valve elements structuring the mitral valve. Further, the tubular part 12 is a part operated by an operator (a medical practitioner) of the catheter for the purpose of inserting the clip part 11 attached to the tip end part 10 up to the mitral valve. To hold the mitral valve, the clip part 11 is separated from the tubular part 12 and is placed (left) in the body of the patient P.

For example, the storage 150 stores therein the shape information and the reflection characteristic information of the tip end part 10 of the catheter. The shape information is information indicating the shape of the tip end part 10 of the catheter. For example, the shape information is information about three-dimensional shapes of the clip part 11 and the tubular part 12 included in the tip end part 10 of the catheter and includes feature amounts related to a degree of oblongness, a degree of spheroidicity, and the like. Further, the reflection characteristic information is information indicating the ultrasound reflection characteristics of the tip end part 10 of the catheter. For example, the reflection characteristic information includes an intensity of a reflected-wave signal observed when a transmission ultrasound wave from the ultrasound probe 101 is reflected by the clip part 11 and an intensity of a reflected-wave signal observed when a transmission ultrasound wave is reflected by the tubular part 12. The intensities of the reflected-wave signals vary depending on the compositions (the materials) of the clip part 11 and the tubular part 12.

The explanations presented above are merely examples. For instance, the storage 150 does not necessarily have to store therein both the shape information and the reflection characteristics. The storage 150 may store therein only one of the two types of information. Further, although FIG. 2 illustrates the example in which the present disclosure is applied to the catheter treatment using the clip, possible embodiments are not limited to this example. For instance, the present disclosure is also applicable to a catheter treatment using an artificial valve. In that situation, the storage 150 stores therein, for example, shape information and reflection characteristic information of a catheter having the artificial valve attached to the tip end thereof. In other words, the tip end part of the catheter includes either the clip part or the artificial valve to be placed with the mitral valve.

Further, the first embodiment is applicable not only to the clip and the artificial valve, but also to a situation where another tool is used, such as an artificial annulus or artificial chordae tendineae. For example, when closing insufficiency has occurred due to an enlargement of the annulus, the artificial annulus is a tool embedded around the annulus so as to cause the enlarged annulus to contract. Further, for example, when closing insufficiency has occurred due to stretching or a rupture of the chordae tendineae, the artificial chordae tendineae is a tool used for connecting together a valve cusp and a papillary muscle (or a part near an apex part of the heart).

The obtaining function 161 is configured to obtain three-dimensional medical image data in which a heart valve of the patient P and a tool inserted into the body of the patient P are imaged by using the ultrasound probe 101. For example, the obtaining function 161 obtains, from the image memory 140, volume data corresponding to the time at which the mitral valve and the tip end part 10 of the catheter are imaged. In this situation, the obtaining function 161 is an example of an obtaining unit. In other words, the obtaining function 161 obtains the three-dimensional medical image data, taken by using the ultrasound probe, of a region including the heart valve of the patient and the catheter inserted into a heart chamber of the patient.

For example, during a catheter treatment of mitral valve closing insufficiency, the operator inserts a TEE probe into the body of the patient P through the mouth of the patient P and performs a three-dimensional scan on a region including the mitral valve. Reflected-wave data acquired during the three-dimensional scan is generated into volume data by the image processing circuitry 130 and is stored into the image memory 140. The obtaining function 161 obtains the volume data stored in the image memory 140.

The above description of the obtaining function 161 is merely an example. For instance, the obtaining function 161 may obtain volume data in which another heart valve is imaged. Alternatively, the obtaining function 161 may obtain volume data in which, for example, a heart valve is imaged by using an arbitrary ultrasound probe other than the TEE probe. Further, the obtaining function 161 may obtain volume data generated as a moving image in units of frames or may obtain a piece of volume data generated as a still image.

The estimating function 162 is configured to estimate a position and a posture of the tool included in the three-dimensional medical image data, by using the shape information and the reflection characteristic information. For example, by using the shape information and the reflection characteristic information stored in the storage 150, the estimating function 162 estimates a position and a posture of the catheter included in the volume data. In this situation, the estimating function 162 is an example of an estimating unit. In the following explanations, the position and the posture may collectively be referred to as the "position/posture".

For example, the estimating function 162 estimates the position and the posture of the tool (the catheter) included in the volume data, by using a coordinate system of the volume data obtained by the obtaining function 161. In this situation, the position of the tool is expressed by, for example, "three-dimensional coordinates of the tip end of the tool" in the coordinate system of the volume data. Further, the posture of the tool is expressed by, for example, "a direction vector indicating the longitudinal direction of the tool".

Figure 3:
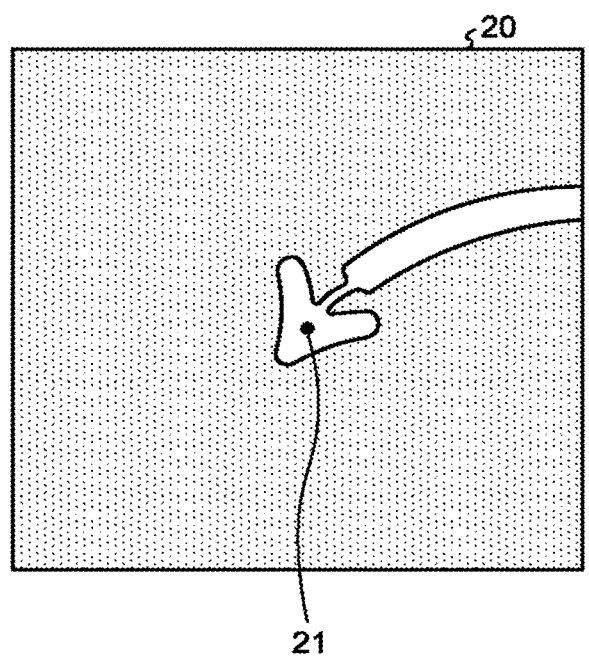
FIG. 3 is a drawing for explaining a process performed by an estimating function according to the first embodiment.

FIG. 3 is a drawing for explaining a process performed by the estimating function 162 according to the first embodiment. FIG. 3 illustrates a binarized image 20 obtained by binarizing the volume data in which the catheter is imaged.

As illustrated in FIG. 3, the estimating function 162 estimates the position and the posture of the catheter by performing an image processing process. For example, by using the reflection characteristic information of the catheter stored in the storage 150, the estimating function 162 binarizes the volume data. In this situation, within an image generated from the ultrasound image data, the catheter inserted in the vicinity of the heart is rendered with brightness levels that are relatively higher than the brightness levels of the heart region. In other words, on the basis of the intensities of the reflected-wave signals reflected by the tip end part 10 of the catheter, the estimating function 162 sets a threshold value for the brightness levels with which it is possible to distinguish the heart region and a catheter region from each other. After that, the estimating function 162 binarizes the volume data by using the set threshold value and generates the binarized image 20 illustrated in FIG. 3. The coordinate system of the binarized image 20 is either the same as or kept in correspondence with the coordinate system of the volume data.

Subsequently, by using the shape information of the catheter stored in the storage 150, the estimating function 162 estimates the position and the posture of the catheter from the binarized image 20. More specifically, the estimating function 162 calculates feature amounts related to the degree of oblongness and the degree of spheroidicity, with respect to a high brightness region included in the binarized image 20. After that, the estimating function 162 extracts a region of the clip part 11 and a region of the tubular part 12 from the binarized image 20, by comparing the calculated feature amounts with the shape information of the clip part 11 and the shape information of the tubular part 12. Subsequently, for example, the estimating function 162 calculates three-dimensional coordinates of a gravity point 21 of the region of the clip part 11 and estimates the calculated three-dimensional coordinates as the position of the catheter. Further, for example, the estimating function 162 calculates a long-axis direction of the region of the clip part 11 and the region of the tubular part 12 and estimates a vector corresponding to the calculated long-axis direction as the posture of the catheter.

In the manner described above, the estimating function 162 estimates the position and the posture of the catheter. In other words, the estimating function 162 estimates the position and the posture of the catheter, by using the factor information indicating how the catheter is rendered in the ultrasound image data.

The above description of the estimating function 162 is merely an example. For instance, the position of the tool may be expressed by three-dimensional coordinates of the tip end of the clip part 11. Further, the posture of the tool may be expressed by a direction vector of the region of the clip part 11. Further, for example, the estimating function 162 does not necessarily have to use both the shape information and the reflection characteristics. For example, the estimating function 162 may estimate the position and posture of the catheter from the volume data, by using only the shape information of the catheter. In other words, the estimating function 162 may estimate the position and the posture of the catheter by using at least one selected from the shape information and the reflection characteristic information.

Alternatively, for example, the estimating function 162 may estimate the position and the posture of the catheter by using mutually-different characteristics (compositions) in two locations positioned apart from each other in the long-axis direction. For example, the estimating function 162 extracts the regions of the clip part 11 and the tubular part 12 from the binarized image 20, by using the shape information of the clip part 11 and the tubular part 12. After that, the estimating function 162 calculates a gravity point with respect to each of the extracted regions of the clip part 11 and the tubular part 12. Subsequently, the estimating function 162 may estimate a direction vector extending from the gravity point of the tubular part 12 to the gravity point of the clip part 11, as the posture of the catheter. Alternatively, for example, the estimating function 162 may estimate the position and the posture of the catheter by using mutually-different characteristics in two locations positioned apart from each other in the short-axis direction of the catheter (the direction orthogonal to the long-axis direction of the catheter). For example, by arranging compositions (materials) having distinctive reflection characteristics to be in positions that are asymmetrical with each other in the short-axis direction of the tubular part 12, it is possible to estimate the position and the posture while taking into consideration the direction along the outer circumference (the circumferential direction) of the tubular part 12.

On the basis of the position and the posture of the tool, the determining function 163 is configured to determine an advancing direction of the tool. For example, on the basis of the position and the posture of the catheter, the determining function 163 determines an advancing direction of the catheter. For example, while using the position of the catheter as the origin, the determining function 163 determines the direction of a vector corresponding to the posture of the catheter as the advancing direction of the catheter. For example, the vector corresponding to the posture of the catheter is a direction vector indicating the longitudinal direction of the catheter. In this situation, the determining function 163 is example of a determining unit. In other words, by using at least one selected from the shape information indicating the shape of the tip end part of the catheter and the reflection characteristic information indicating the ultrasound reflection characteristics of the tip end part, the determining function 163 determines the advancing direction of the tip end part by obtaining information on the position and the posture of the tip end part included in the three-dimensional medical image data.

In the example illustrated in FIG. 3, the determining function 163 determines the three-dimensional coordinates of the gravity point 21 of the clip part 11 as the origin. After that, the determining function 163 determines the direction of the vector corresponding to the posture of the catheter and being originated from the determined origin, as the advancing direction of the catheter.

The above description of the determining function 163 is merely an example. For instance, the determining function 163 may calculate the gravity point of the regions of the clip part 11 and the tubular part 12 as the position of the catheter. After that, the determining function 163 may determine the advancing direction of the catheter by using the calculated gravity point of the regions of the clip part 11 and the tubular part 12 as the origin. Alternatively, for example, by using the gravity point of the tubular part 12 as the origin, the determining function 163 may calculate a direction vector extending from the origin to the gravity point of the clip part 11 as the posture of the catheter. After that, the determining function 163 may determine the calculated direction vector as the advancing direction. In this situation, because the catheter as a whole advances while meandering inside the body of the patient, it is desirable to calculate the advancing direction on the basis of the position/posture of a tip end region of the catheter.

The generating function 164 is configured to generate a display image from the three-dimensional medical image data, in accordance with the position and the advancing direction of the tool. For example, the generating function 164 generates, as the display image, a Volume Rendering (VR) image that uses a position based on the position of the tool as a point of view and uses the advancing direction of the tool as a line of sight. In this situation, the generating function 164 is an example of a generating unit. In other words, the generating function 164 generates the display image from the three-dimensional medical image data, on the basis of the position and the advancing direction of the tip end part. Further, the display image is an image expressing the three-dimensional medical image data in a three-dimensional manner.

Figure 4:
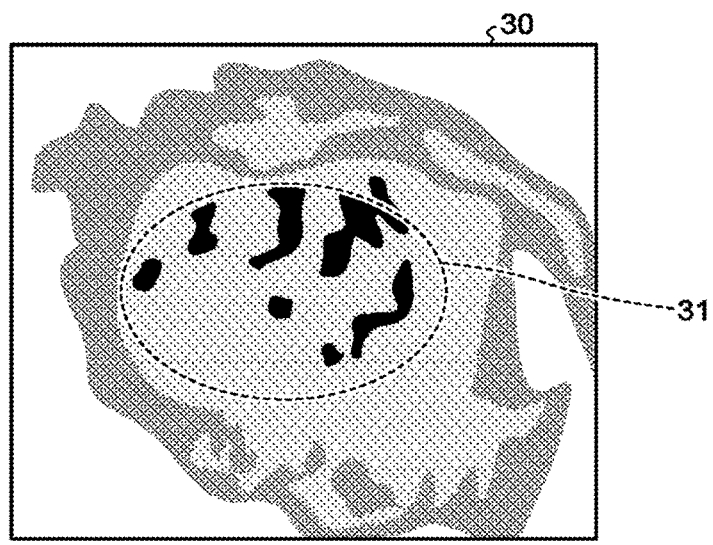
FIG. 4 is a drawing illustrating an example of a display image generated by a generating function according to the first embodiment.

FIG. 4 is a drawing illustrating an example of the display image generated by the generating function 164 according to the first embodiment. FIG. 4 illustrates a VR image 30 that uses the position of the tip end part 10 of the catheter as the point of view and uses the advancing direction of the catheter as the line of sight. In this situation, because the tip end part 10 of the catheter inserted in a blood vessel of the patient P is used as the point of view, the VR image 30 is rendered as if the vascular lumen and the heart valve were viewed from the inside of the blood vessel.

As illustrated in FIG. 4, the generating function 164 generates the VR image 30, for example, by performing a VR process on the volume data obtained by the obtaining function 161. In this situation, the generating function 164 sets the point of view and the line of sight of the VR process on the basis of the position and the advancing direction of the catheter. For example, the generating function 164 sets the gravity point 21 of the clip part 11 estimated by the estimating function 162 as the position of the tip end part 10 of the catheter, as the point of view of the VR process. Further, the generating function 164 sets the direction vector determined by the determining function 163 as the advancing direction of the catheter, as the line of sight of the VR process. Further, by using the point of view and the line of sight of the VR process that were set, the generating function 164 generates the VR image 30 serving as the display image, by performing the VR process on the volume data.

In this situation, because the VR image 30 is an image that uses the position of the tip end part 10 of the catheter as the point of view and uses the advancing direction of the catheter as the line of sight, the VR image 30 is an image that appears as if the viewer was looking into the vascular lumen positioned in the advancing direction from the tip end part 10 of the catheter. When the mitral valve is positioned in the advancing direction, the mitral valve is rendered in the VR image 30 as illustrated in a region 31 in FIG. 4. When the mitral valve is positioned outside of the advancing direction of the catheter, the position of the mitral valve may also be rendered in an outside position or may not be rendered at all.

As explained above, on the basis of the position and the advancing direction of the catheter, the generating function 164 generates the display image from the volume data. The above description of the generating function 164 is merely an example. For instance, the generating function 164 does not necessarily have to set the position of the catheter itself as the point of view of the VR process. For example, the generating function 164 may set an arbitrary position based on the position of the catheter as the point of view of the VR process. For example, the generating function 164 may set a position away from the tip end of the catheter by a predetermined distance in the advancing direction as the point of view of the VR process. With this arrangement, when a position diagonally behind the advancing direction of the catheter is used as the point of view, the catheter itself is rendered in the VR image. It is therefore possible to easily understand the positional relationship between the tip end part of the catheter and the structure of the heart positioned in the advancing direction. Further, for example, when the position of the catheter itself is used as the point of view, the VR image moves around vigorously when the catheter is being moved vigorously. In that situation, there is a possibility that visibility of the VR image may be degraded significantly. In contrast, when the position of the catheter itself is not used as the point of view, it is possible to provide a stable VR image even when the catheter is being moved vigorously. In these situations, the display image generated by the generating function 164 does not necessarily have to be the VR image and may be, for example, a surface rendering image regarding a surface position of the bio tissue such as mitral valves detected in a binarized image.

In other words, the display image is one selected from between a volume rendering image and a surface rendering image. Further, in those situations, the display image is the one selected from between the volume rendering image and the surface rendering image generated by using a point of view based on the position of the tip end part and a line of sight based on the advancing direction of the tip end part.

The display controlling function 165 is configured to cause the display image to be displayed. For example, the display controlling function 165 causes the display 103 to display the VR image 30 generated by the generating function 164. In this situation, the display controlling function 165 is an example of a display controlling unit. In recent years, a method for exerting a higher stereoscopic effect is known by which a VR image is displayed with a shadow behind a structure observed when a light source that is set is applied to the structure. In the first embodiment, by setting a light source in such a manner that a shadow of the catheter is rendered over an image of a valve or a cardiac muscle, it is expected that additional information is provided for the understanding of the positional relationship. It is therefore possible to use a VR image that implements such a publicly-known method at the same time.

The above description of the display controlling function 165 is merely an example. For instance, together with the VR image 30, the display controlling function 165 may simultaneously display a cross-sectional view taken on an arbitrary cross-sectional plane in the volume data or an X-ray fluoroscopic image taken during a surgical operation. Other examples of possible display modes will be explained later in the description of the other embodiments and modification examples.

Figure 5:
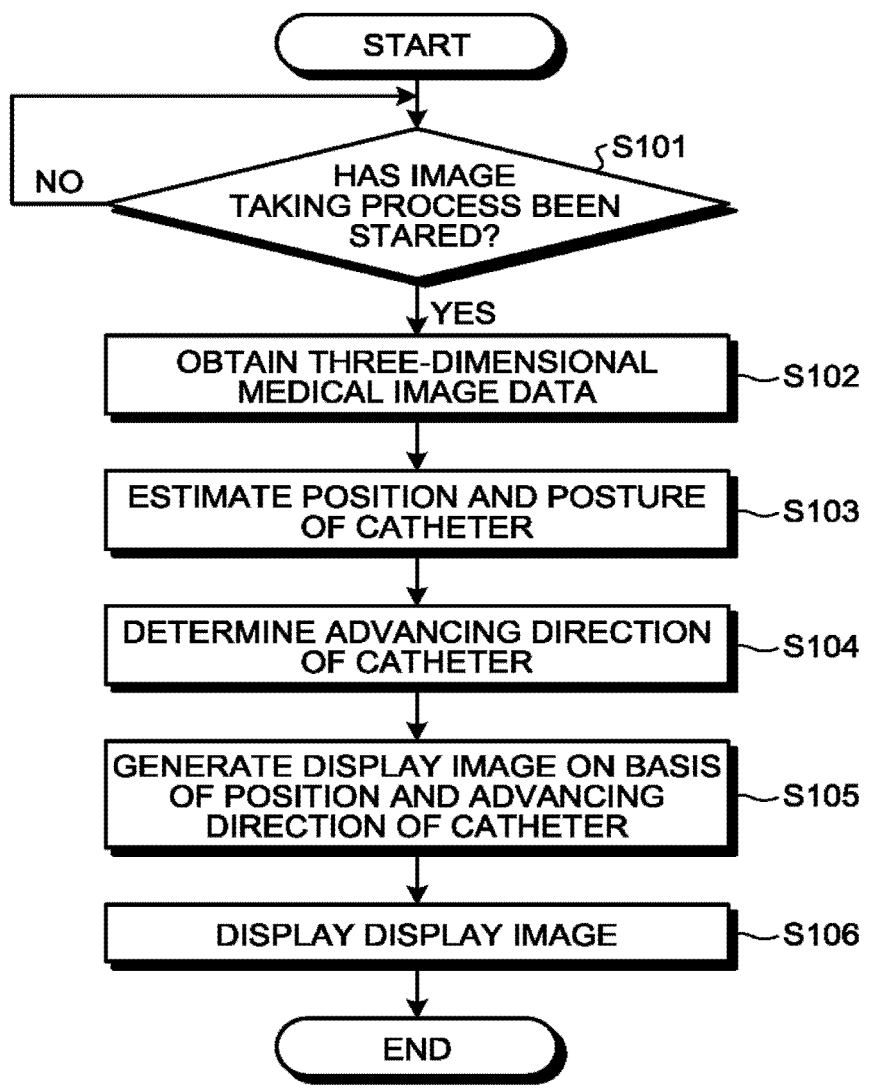
FIG. 5 is a flowchart illustrating a processing procedure performed by the ultrasound diagnosis apparatus according to the first embodiment.

FIG. 5 is a flowchart illustrating a processing procedure performed by the ultrasound diagnosis apparatus 1. For example, the processing procedure illustrated in FIG. 5 is started when an instruction to start an image taking process is received from the operator.

At step S101, it is judged whether an image taking process is started. For example, the input device 102 receives an instruction to start an image taking process from the operator and transmits the received instruction to the processing circuitry 160 included in the apparatus main body 100. When having received the instruction transmitted thereto by the input device 102, the processing circuitry 160 determines that an image taking process is started (step S101: Yes), and the processes at step S102 and thereafter are started. On the contrary, when no image taking process has been started (step S101: No), the processes at step S102 and thereafter are not started, and the processing functions of the processing circuitry 160 are in a standby state.

When the judgment result at step S101 is in the affirmative, the obtaining function 161 obtains the three-dimensional medical image data (the volume data) at step S102. For example, the obtaining function 161 obtains the volume data in which the mitral valve and the tip end part 10 of the catheter are imaged, from the image memory 140.

At step S103, the estimating function 162 estimates the position and the posture of the catheter. For example, by using the shape information and the reflection characteristic information of the catheter stored in the storage 150, the estimating function 162 estimates the position and the posture of the catheter included in the volume data. More specifically, the estimating function 162 generates the binarized image 20 by binarizing the volume data while using the reflection characteristic information of the catheter. After that, the estimating function 162 extracts a region of the catheter from the binarized image 20 by calculating feature amounts related to the degree of oblongness, the degree of spheroidicity, and the like, with respect to a high brightness region included in the binarized image 20 and comparing the feature amounts with the shape information of the catheter. After that, on the basis of three-dimensional coordinates of the extracted catheter region, the estimating function 162 estimates the position and the posture of the catheter.

At step S104, the determining function 163 determines an advancing direction of the catheter. For example, on the basis of the position and the posture of the catheter estimated by the estimating function 162, the determining function 163 determines the advancing direction of the posture of the catheter. More specifically, while using the position of the catheter as the origin, the determining function 163 determines the direction of a vector corresponding to the posture of the catheter, as the advancing direction of the catheter.

At step S105, the generating function 164 generates a display image on the basis of the position and the advancing direction of the catheter. For example, the generating function 164 generates the VR image 30 serving as the display image by performing a VR process on the volume data, the VR process using the position of the catheter as a point of view and using the advancing direction of the catheter as a line of sight.

At step S106, the display controlling function 165 causes the display image to be displayed. For example, the display controlling function 165 causes the display 103 to display the VR image 30 generated by the generating function 164.

As explained above, from the volume data, the ultrasound diagnosis apparatus 1 generates and displays the VR image 30 that uses the position of the catheter as the point of view and uses the advancing direction of the catheter. Although FIG. 5 illustrates the processing procedure for displaying the VR image 30 represented by a still image, the processing procedure is also applicable to a situation where the VR image 30 is displayed as a moving image. When the VR image 30 is displayed as a moving image, the processing circuitry 160 repeatedly performs the processes at steps S102 through S106, until an instruction to end the image taking process is received.

As explained above, in the ultrasound diagnosis apparatus 1, the obtaining function 161 obtains the volume data in which the mitral valve (the heart valve) and the tool (the catheter) are imaged. Further, the estimating function 162 estimates the position and the posture of the tool included in the volume data by using the shape information and the reflection characteristic information of the tool. Further, the determining function 163 determines the advancing direction of the posture of the tool, on the basis of the position and the posture of the tool. After that, the generating function 164 generates the display image on the basis of the position and the advancing direction of the tool. Subsequently, the display controlling function 165 causes the display image to be displayed. With these arrangements, the ultrasound diagnosis apparatus 1 according to the first embodiment is able to generate the display image that makes it possible to view the position and the advancing direction of the tool with respect to the heart valve.

In other words, the ultrasound diagnosis apparatus 1 according to the first embodiment generates the VR image 30 by performing the VR process that uses the position of the tip end part 10 of the catheter as the point of view and uses the advancing direction of the catheter as the line of sight. As a result, the ultrasound diagnosis apparatus 1 is able to display the VR image 30 that appears as if the viewer was looking into the vascular lumen positioned in the advancing direction from the tip end part 10 of the catheter. In an example, the ultrasound diagnosis apparatus 1 is able to display an image that appears as if the viewer was going through the vascular lumen toward the mitral valve, by expressing in images in a real-time manner how the operator moves the catheter toward the mitral valve. Further, in accordance with operations of the operator to advance and retract the catheter, the point of view and the line of sight used for rending the vascular lumen change. Accordingly, the operator is able to intuitively understand the movements of the catheter in the vascular lumen. Consequently, when moving the catheter toward the mitral valve, the operator is able to operate the catheter with a feeling as if he/she was putting a thread through the eye of a sewing needle. As a result, it becomes easy for the operator to arrange the clip part 11 attached to the tip end part 10 of the catheter to be placed with (to be held onto) the mitral valve. It is therefore possible to improve the level of precision of the treatment while shortening the period of time required by the catheter treatment.

Further, for example, the ultrasound diagnosis apparatus 1 according to the first embodiment is configured to estimate the position/posture of the tool rendered in the image, by using the factor information (the shape information and the reflection characteristic information) indicating the factors related to how the tool is rendered in the ultrasound image data. Accordingly, for example, even when the tool itself has a characteristic of meandering in the body of the patient like the catheter does, the ultrasound diagnosis apparatus 1 is able to accurately estimate the position/posture of the tool. More specifically, the ultrasound diagnosis apparatus 1 estimates the position/posture of the tool, by using the mutually-different characteristics in the two locations positioned apart from each other in the long-axis direction of the tool such as the clip part 11 and the tubular part 12 included in the tip end part 10. Consequently, the ultrasound diagnosis apparatus 1 is able to accurately determine the advancing direction of the tool that serves as the line of sight of the VR process.

First Modification Example of First Embodiment

In the first embodiment, the example is explained in which the ultrasound diagnosis apparatus 1 displays the VR image 30 as the display image; however, possible embodiments are not limited to this example. For instance, the ultrasound diagnosis apparatus 1 may generate a cross-sectional image (an MPR image).

The generating function 164 generates a cross-sectional image taken along the advancing direction of the tool as a display image. For example, the generating function 164 generates cross-sectional images taken on two cross-sectional planes that are orthogonal to each other and extend along the advancing direction of the catheter determined by the determining function 163.

Figure 6:
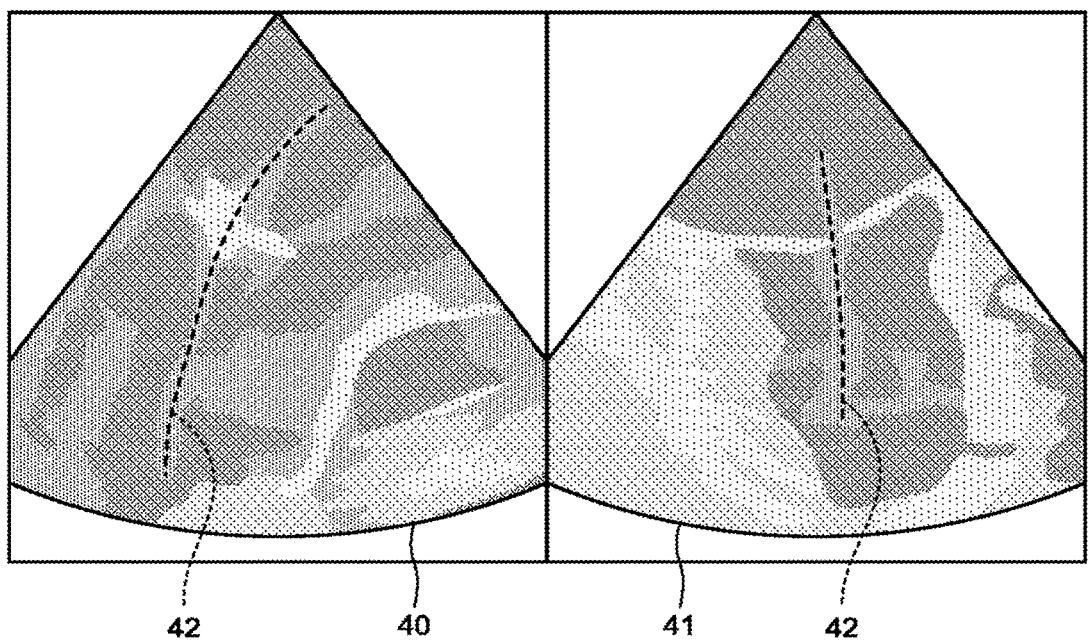
FIG. 6 is a drawing illustrating an example of a display image generated by a generating function according to a first modification example of the first embodiment.

FIG. 6 is a drawing illustrating an example of the display image generated by the generating function 164 according to a first modification example of the first embodiment. FIG. 6 illustrates a cross-sectional image 40 in a predetermined direction extending along the advancing direction of the catheter and a cross-sectional image 41 being orthogonal to the cross-sectional image 40 and extending along the advancing direction.

As illustrated in FIG. 6, the generating function 164 generates the cross-sectional image 40 and the cross-sectional image 41. In this situation, because the cross-sectional image 40 and the cross-sectional image 41 both extend along the advancing direction of the catheter, a catheter 42 is rendered in each of the images.

Further, the display controlling function 165 causes the display 103 to display the cross-sectional image 40 and the cross-sectional image 41 generated by the generating function 164, as display images. In that situation, the display controlling function 165 may cause the display 103 to display the VR image 30, the cross-sectional image 40, and the cross-sectional image 41 simultaneously or to display the cross-sectional image 40 and the cross-sectional image 41 without displaying the VR image 30.

In the manner described above, the ultrasound diagnosis apparatus 1 generates and displays the cross-sectional images taken along the advancing direction of the tool. With this arrangement, because the cross-sectional images render the tool, the ultrasound diagnosis apparatus 1 is able to display the positional relationship between the tool and a structure such as the heart valve in an easy-to-understand manner.

The above descriptions of the generating function 164 and the display controlling function 165 are merely examples. For instance, the generating function 164 does not necessarily have to generate the two cross-sectional images that are orthogonal to each other and extend along the advancing direction of the catheter. More specifically, the cross-sectional image 40 and the cross-sectional image 41 generated by the generating function 164 do not necessarily have to be taken on orthogonal cross-sectional planes, but may be taken on cross-sectional planes that intersect each other at an arbitrary angle. Further, the cross-sectional images generated by the generating function 164 do not necessarily have to be taken on two cross-sectional planes, but may be taken on any arbitrary number of cross-sectional planes. Furthermore, the generating function 164 does not necessarily have to be cross-sectional images taken along the advancing direction of the tool, but may be, for example, an apical four-chamber (A4C) image, an apical two-chamber (A2C) image, or the like.

Second Modification Example of First Embodiment

Further, for example, the ultrasound diagnosis apparatus 1 may display an X-ray image taken during a catheter treatment, together with the display image.

For example, during catheter treatments, there are many situations where a fluoroscopy process is performed on the patient P by using an X-ray diagnosis apparatus, in addition to a process of acquiring ultrasound image data using a TEE probe. In those situations, in the ultrasound diagnosis apparatus 1, the display controlling function 165 causes an X-ray image to be displayed simultaneously with the display image, the X-ray image being generated on the basis of X-rays that have passed through the patient P. More specifically, the display controlling function 165 obtains a fluoroscopic image (the X-ray image) taken by the X-ray diagnosis apparatus and causes the display 103 to simultaneously display the obtained fluoroscopic image together with the VR image 30 and/or the cross-sectional images 40 and 41.

In the manner described above, the ultrasound diagnosis apparatus 1 displays the X-ray image together with the display image. In many situations, medical doctors who perform catheter treatments are used to viewing X-ray images, it is expected that the efficiency of the medical doctors in interpreting the images can be improved.

Third Modification Example of First Embodiment

Further, in the first embodiment, the example is explained in which the ultrasound diagnosis apparatus 1 generates the VR image 30 from a first-person point of view; however, possible embodiments are not limited to this example. The ultrasound diagnosis apparatus 1 may be provided with a configuration capable of generating a VR image from a third-person point of view or a configuration capable of switching between a VR image from a first-person point of view and a VR image from a third-person point of view. In this situation, the "first-person point of view" denotes a view from the position of the tool and, generally speaking, the tool itself is not rendered in the view. In contrast, the "third-person point of view" denotes a view from a position other than the position of the tool, and the tool itself is also rendered in the view. The third-person point of view is realized by using a position behind the tool as a point of view.

The generating function 164 generates a VR image by performing a VR process while using a position behind the tip end of the tool as a point of view. For example, the generating function 164 performs the VR process by using a position behind the tip end part 10 of the catheter at a predetermined distance as the point of view of the VR process.

Figure 7:
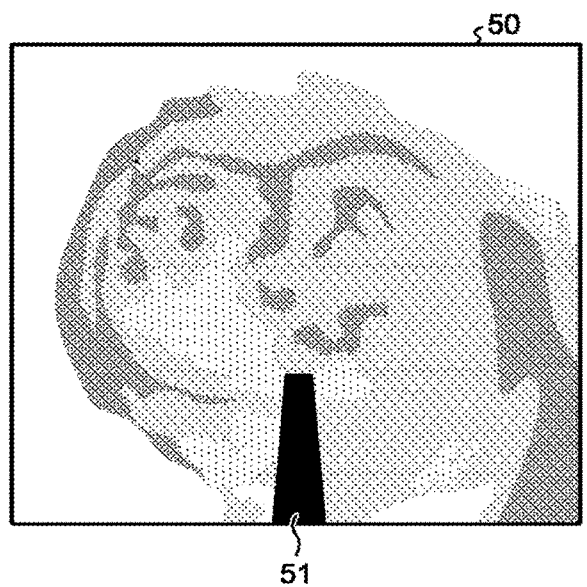
FIG. 7 is a drawing illustrating an example of a display image generated by a generating function according to a third modification example of the first embodiment.

FIG. 7 is a drawing illustrating an example of a display image generated by the generating function 164 according to a third modification example of the first embodiment. FIG. 7 illustrates a VR image 50 that uses the advancing direction of the catheter as a line of sight and uses a position behind the tip end part 10 of the catheter at a predetermined distance as a point of view.

As illustrated in FIG. 7, the generating function 164 generates the VR image 50 by performing the VR process that uses the advancing direction of the catheter as the line of sight and uses the position behind the tip end part 10 of the catheter at the predetermined distance as the point of view. As a result, the generating function 164 generates, for example, the VR image 50 rending an image 51 of the tip end of the catheter.

Further, in accordance with an instruction from the operator, the generating function 164 switches between generating a VR image from a first-person point of view and generating a VR image from a third-person point of view. In other words, in accordance with instructions from the operator, the generating function 164 generates one selected from between: the VR image that uses the tip end of the tool as the point of view; and the VR image that uses the position behind the tip end of the tool as the point of view.

In the manner described above, the ultrasound diagnosis apparatus 1 may be provided with the configuration capable of generating the VR image from the third-person point of view and the configuration capable of switching between the VR image from the first-person point of view and the VR image from the third-person point of view. With this arrangement, for example, the operator is able to have a VR image displayed by selecting a point of view which he/she considers to provide an easy-to-see image.

Second Embodiment

For example, the ultrasound diagnosis apparatus 1 is further capable of displaying an image for guiding a tool to a position and a posture in and with which the tool should be installed.

Figure 8:
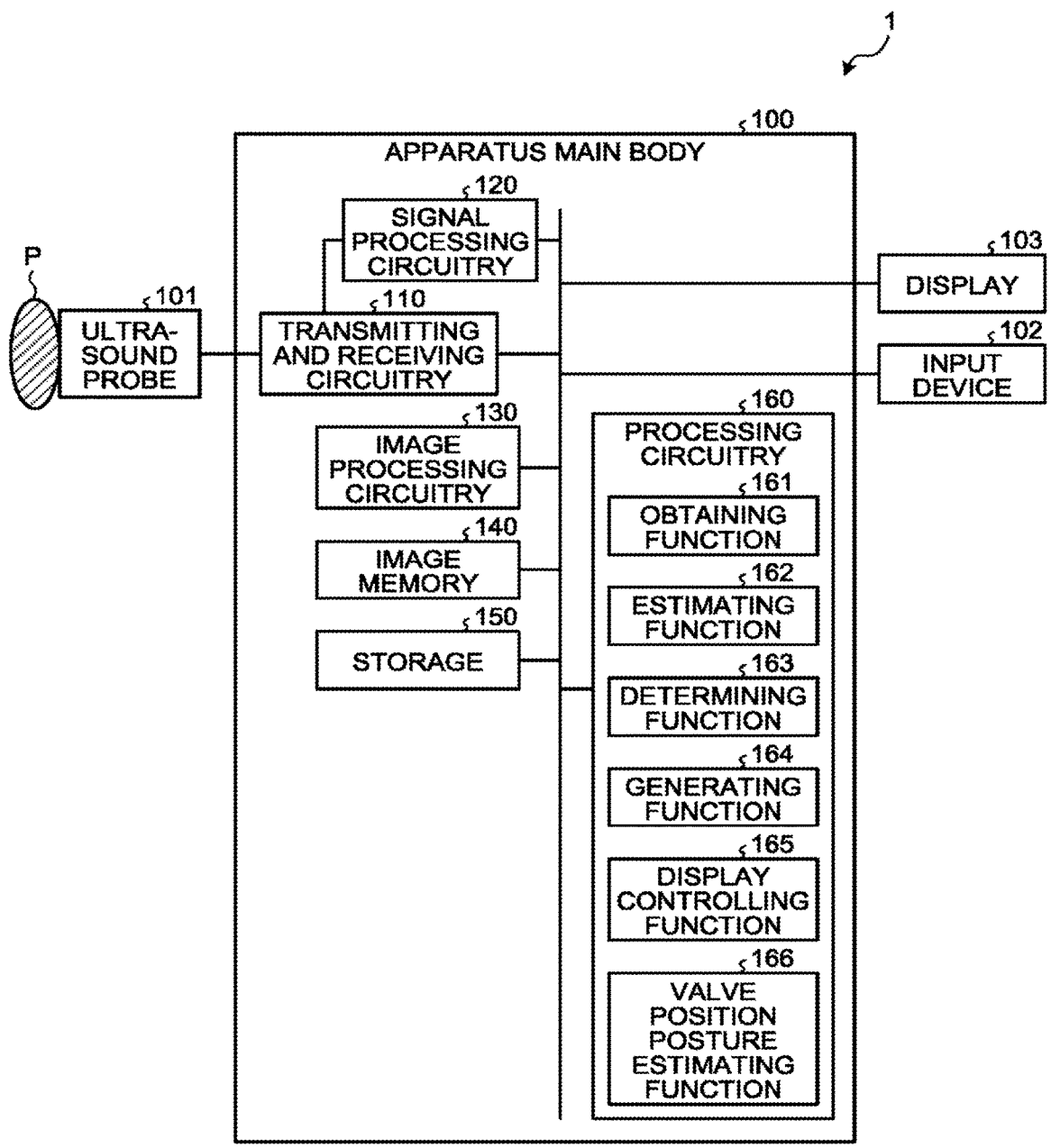
FIG. 8 is a block diagram illustrating an example of an ultrasound diagnosis apparatus according to a second embodiment.

FIG. 8 is a block diagram illustrating an example of the ultrasound diagnosis apparatus 1 according to a second embodiment. The ultrasound diagnosis apparatus 1 according to the second embodiment has a similar configuration to that of the ultrasound diagnosis apparatus 1 illustrated in FIG. 1 and is different in that the processing circuitry 160 further includes a valve position posture estimating function 166. Thus, as for the second embodiment, the explanation will focus on some of the features that are different from those in the first embodiment. The features having the same functions as those explained in the first embodiment will be referred to by using the same reference characters as those in FIG. 1, and the explanations thereof will be omitted.

The valve position posture estimating function 166 is configured to estimate a position and a posture in and with which a tool should be installed, with respect to the position and the posture of a heart valve. The position and the posture in and with which the tool should be installed with respect to the position and the posture of the heart valve may be referred to as the "position/posture of the valve".

First, the estimating function 162 estimates the position and the posture of the heart valve of the patient P in the three-dimensional medical image data. For example, the estimating function 162 extracts feature points included in the volume data, by using a supervised machine learning algorithm. In this situation, the supervised machine learning algorithm has been constructed by using a plurality of supervision images in which a plurality of feature points included in the heart valve are properly positioned. Further, by comparing a model indicating a three-dimensional positional relationship among the plurality of feature points included in the heart valve with the extracted feature points, the estimating function 162 estimates the position and the posture of the heart valve.

After that, with respect to the position and the posture of the heart valve, the valve position posture estimating function 166 estimates a position and a posture (a position/posture of the valve) in and with which the tool should be installed. For example, the valve position posture estimating function 166 estimates the position/posture of the valve, by using a model of a three-dimensional positional relationship corresponding to when the tool is properly installed with respect to the heart valve. More specifically, the valve position posture estimating function 166 estimates the position and the posture in and with which the tool should be installed, by fitting the model of the three-dimensional positional relationship corresponding to when the tool is properly installed with respect to the heart valve, to the position and the posture of the heart valve estimated by the estimating function 162.

Figure 9:
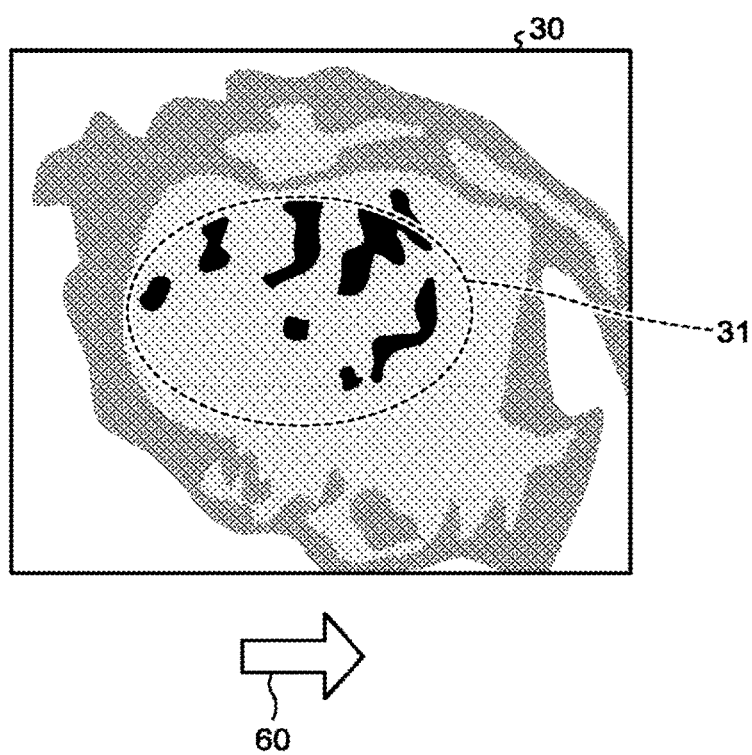
FIG. 9 is a drawing illustrating an example of a display image displayed by a display controlling function according to the second embodiment.

After that, the display controlling function 165 causes an image to be displayed simultaneously with the display image, the image indicating a direction in which the position and the posture of the tool estimated by the estimating function 162 move toward and away from the position and the posture of the tool to be installed estimated by the valve position posture estimating function 166. FIG. 9 is a drawing illustrating an example of the display image displayed by the display controlling function 165 according to the second embodiment. FIG. 9 illustrates an arrow image 60 indicating a direction that brings the current position/posture of the catheter closer to the position/posture in and with which the catheter should be installed.

As illustrated in FIG. 9, by using three-dimensional coordinates of the current position/posture of the catheter and three-dimensional coordinates of the position/posture in and with which the tool should be installed, the display controlling function 165 determines the direction that brings the current position/posture of the catheter closer to the position/posture in and with which the catheter should be installed. After that, the display controlling function 165 generates the arrow image 60 indicating the determined direction and displays the generated arrow image 60 together with the current VR image 30.

As explained above, the ultrasound diagnosis apparatus 1 is capable of displaying the image indicating the direction that brings the tool closer to the position/posture in and with which the tool (the catheter) should be installed. Accordingly, the operator is able to intuitively understand, for example, the direction in which the catheter should be positioned. The descriptions of the first embodiment and the modification examples thereof are also applicable to the second embodiment.

A Modification Example of Second Embodiment

Further, for example, the ultrasound diagnosis apparatus 1 may display a direction in which the tool has actually moved (a moving direction), together with the display image.

Figure 10:
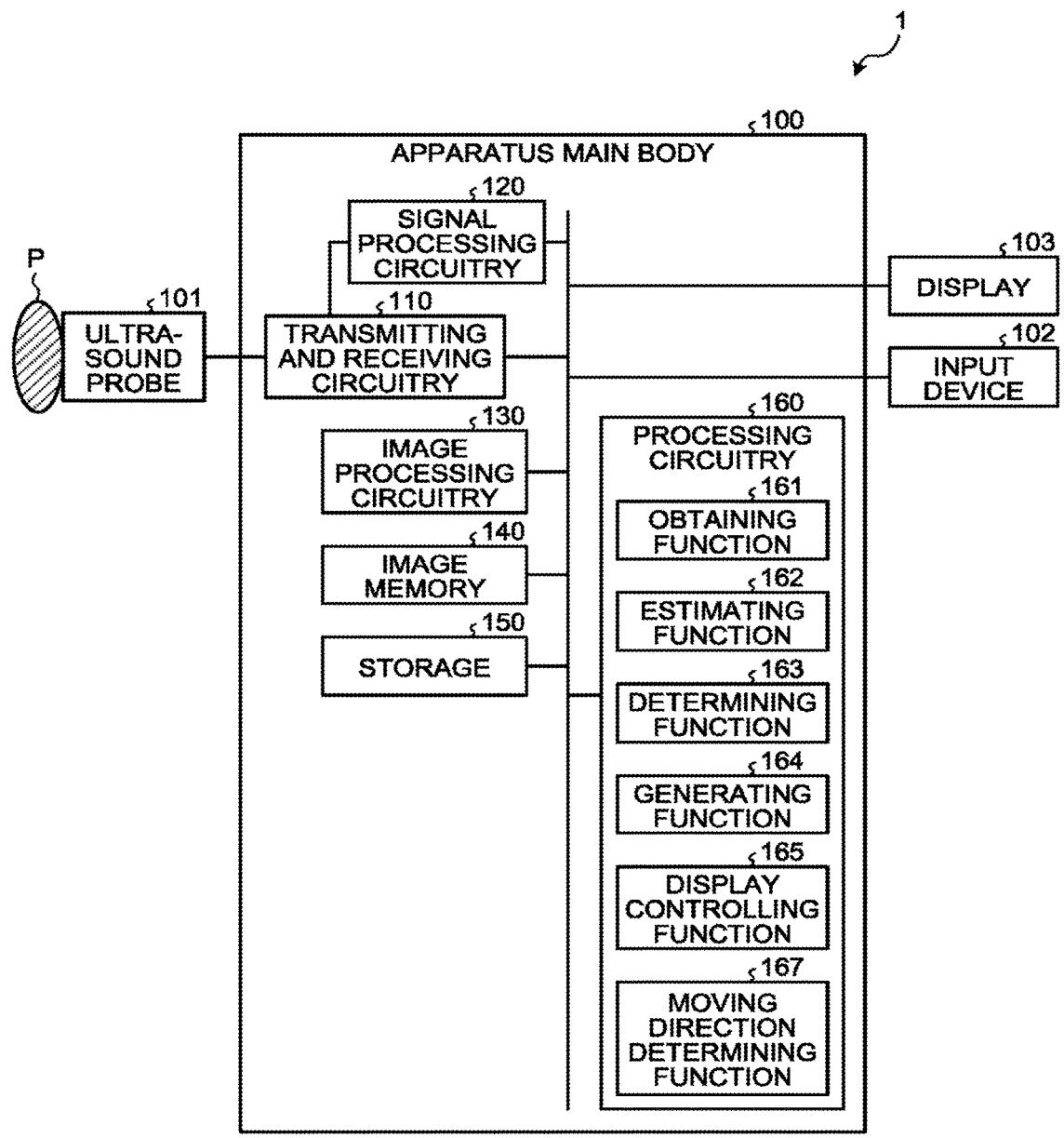
FIG. 10 is a block diagram illustrating an example of an ultrasound diagnosis apparatus according to a modification example of the second embodiment.

FIG. 10 is a block diagram illustrating an example of the ultrasound diagnosis apparatus 1 according to a modification example of the second embodiment. The ultrasound diagnosis apparatus 1 according to the modification example of the second embodiment has a similar configuration to that of the ultrasound diagnosis apparatus 1 illustrated in FIG. 1 and is different in that the processing circuitry 160 further includes a moving direction determining function 167. Thus, as for the modification example of the second embodiment, the explanation will focus on some of the features that are different from those in the first embodiment. The features having the same functions as those explained in the first embodiment will be referred to by using the same reference characters as those in FIG. 1, and the explanations thereof will be omitted.

The moving direction determining function 167 is configured to determine a moving direction of the tool on the basis of positions of the tool at mutually-different times. Further, the display controlling function 165 causes an image indicating the moving direction of the tool determined by the moving direction determining function 167 to be displayed simultaneously with the display image.

For example, the moving direction determining function 167 determines the moving direction of the tool in a coordinate system of the volume data, by using the position of the tool in each of pieces of volume data in a time-series. More specifically, on the basis of the three-dimensional coordinates of the tip end part 10 of the catheter in the volume data of the current frame and the three-dimensional coordinates of the tip end part 10 of the catheter in the volume data of the immediately preceding frame, the moving direction determining function 167 determines the moving direction of the tip end part 10 of the catheter as derived from the immediately preceding frame. Further, the display controlling function 165 causes the image indicating the moving direction of the tool determined by the moving direction determining function 167 to be displayed simultaneously with the display image. In this situation, because the image indicating the moving direction is, for example, the same as or similar to the arrow image 60 illustrated in FIG. 9, the illustration thereof is omitted from the drawings.

As explained above, the ultrasound diagnosis apparatus 1 displays the direction in which the tool has actually moved, together with the display image. Accordingly, for example, the operator is able to intuitively understand how the catheter has actually moved within the display image, as a result of him/her moving the catheter.

The above description is merely an example. For instance, the display controlling function 165 may display the image (the arrow image 60 in FIG. 9) indicating the direction that brings the catheter closer to the position/posture in and with which the catheter should be installed, together with the image indicating the actual moving direction of the catheter. With this arrangement, the operator is able to quickly understand whether the direction in which the tool should be positioned coincides with the actual moving direction of the tool.

Third Embodiment

For example, the ultrasound diagnosis apparatus 1 is further capable of displaying, on the basis of a result of a pre-surgical-operation simulation, a locus of a movement up to the time when the tool is positioned in the position and the posture in and with which the tool should be installed.

The ultrasound diagnosis apparatus 1 according to the third embodiment has a similar configuration to that of the ultrasound diagnosis apparatus 1 illustrated in FIG. 1 and is different for the contents of the processes performed by the processing circuitry 160. Thus, as for the third embodiment, the explanation will focus on some of the features that are different from those in the first embodiment. The illustration of the features having the same functions as those explained in the first embodiment will be omitted from the drawings.

From a result of a pre-surgical-operation simulation performed on the patient P, the obtaining function 161 obtains a locus of the movement up to the time when the tool is installed with a heart valve of the patient P. In this situation, the pre-surgical-operation simulation is a simulation performed prior to a catheter treatment and may be performed, for example, by using a Computed Tomography (CT) image taken in advance. As a result of the pre-surgical-operation simulation, for example, a locus of the movement up to the time when the catheter is installed with the mitral valve of the patient P is output. From the result of the pre-surgical-operation simulation, the obtaining function 161 obtains the locus of the movement up to the time when the catheter is installed with the mitral valve of the patient P. In this situation, the locus of the movement is information expressed with a coordinate system of the CT image used in the pre-surgical-operation simulation.

By aligning the position of the locus of the movement with the position of the three-dimensional medical image data, the display controlling function 165 causes an image for guiding the advancing course of the tool to be displayed. For example, by aligning the position of the CT image used in the pre-surgical-operation simulation with the position of the volume data taken by the TEE probe, the display controlling function 165 transforms the coordinate system of the locus of the movement into the coordinate system of the volume data. Further, the display controlling function 165 generates an image for guiding the advancing course of the tool, by using the locus of the movement resulting from the coordinate transformation. In one example, as the image for guiding the advancing course of the tool, the display controlling function 165 displays an image of a line (or an image of a broken line) indicating the locus of the movement so as to be superimposed over the VR image 30 illustrated in FIG. 4. In another example, as the image for guiding the advancing course of the tool, the display controlling function 165 displays an image of a line indicating the locus of the movement so as to be superimposed over the cross-sectional images 40 and 41 illustrated in FIG. 6.

In the manner described above, the ultrasound diagnosis apparatus 1 displays the image for guiding the advancing course of the tool. With this arrangement, the operator is able to view the locus of the movement up to the time when the tool is positioned in the position and the posture in and with which the tool should be installed.

A Modification Example of Third Embodiment

For example, the ultrasound diagnosis apparatus 1 is further capable of making a judgment and providing information about an extent appropriate for the placement of the tool in the body of the patient P (hereinafter, simply "the placement of the tool").

Figure 11:
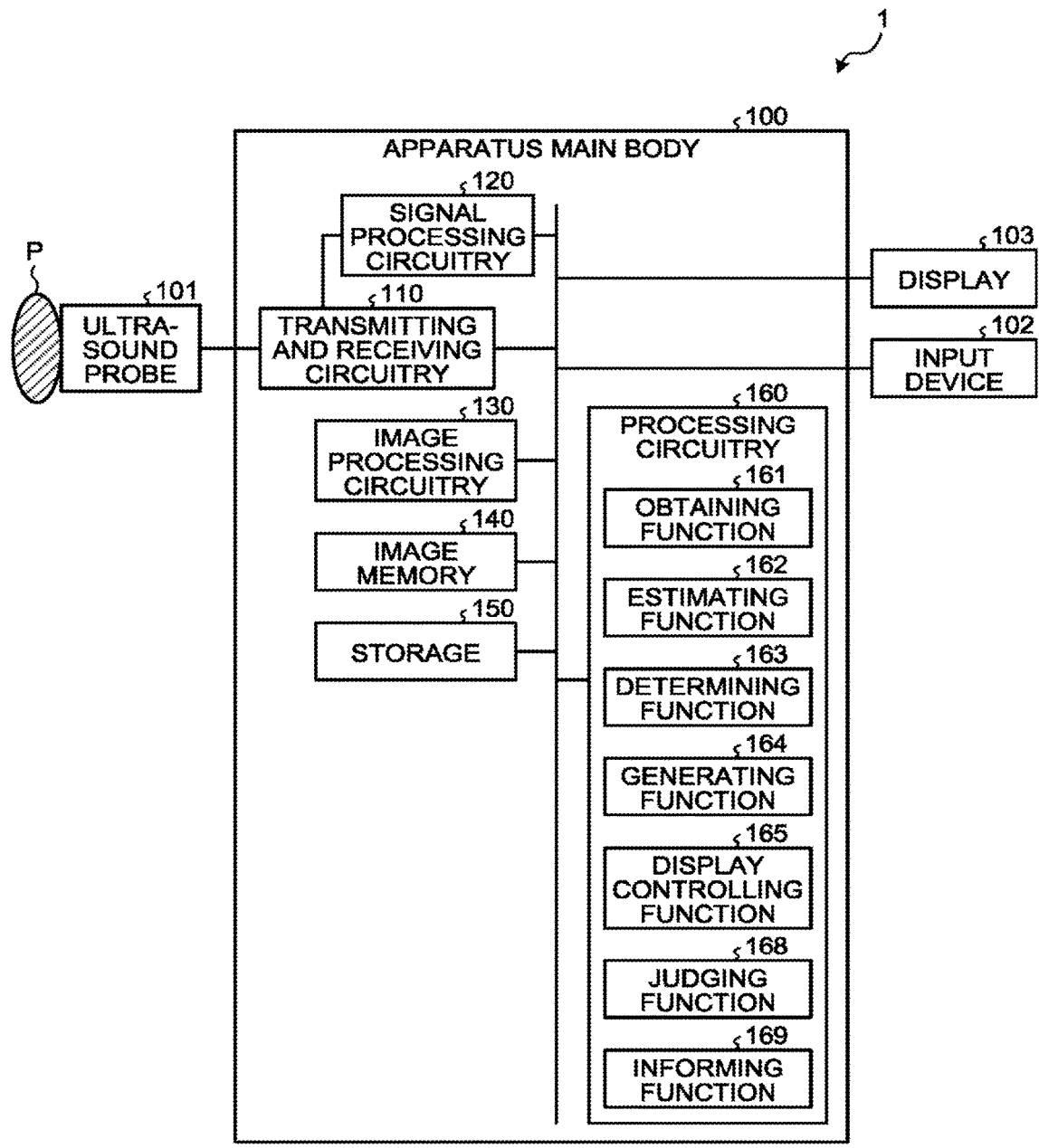
FIG. 11 is a block diagram illustrating an example of an ultrasound diagnosis apparatus according to a modification example of a third embodiment.

FIG. 11 is a block diagram illustrating an example of the ultrasound diagnosis apparatus 1 according to a modification example of the third embodiment. The ultrasound diagnosis apparatus 1 according to the modification example of the third embodiment has a similar configuration to that of the ultrasound diagnosis apparatus 1 illustrated in FIG. 1 and is different in that the processing circuitry 160 further includes a judging function 168 and an informing function 169. Thus, as for the modification example of the third embodiment, the explanation will focus on some of the features that are different from those in the first embodiment. The features having the same functions as those explained in the first embodiment will be referred to by using the same reference characters as those in FIG. 1, and the explanations thereof will be omitted.

The judging function 168 is configured to judge a degree of appropriateness of the placing position of the tip end part on the basis of a model of movements of a heart valve obtained from a pre-surgical-operation simulation on the patient. In this situation, during the pre-surgical-operation simulation, for example, a locus of the movements of the heart valve may be calculated in advance as a motion model. The motion model of the heart valve is a model of the movements of the heart valve of the patient P, the heart valve moving due to heartbeats. For example, the motion model may include patterns of various states caused by the movements of the heart, such as a state in which the heart valve is closed and a state in which the heart valve open.

For example, the judging function 168 compares the volume data taken by the TEE probe with the motion model of the heart valve, by performing a pattern recognition process. After that, the judging function 168 calculates a likelihood value (a level of similarity) with respect to a pattern corresponding to the state in which the heart valve is closed (hereinafter, "heart valve closed state").

The informing function 169 is configured to provide information about a result of the judgment made by the judging function 168. For example, on the basis of the likelihood value with respect to the pattern corresponding to the heart valve closed state calculated by the judging function 168, the informing function 169 provides information about the extent appropriate for the placement of the tool. For example, the informing function 169 causes the display 103 to display the calculated likelihood value as the extent appropriate for the placement of the tool. Alternatively, for example, the informing function 169 may cause the display 103 to display a score (an evaluation) corresponding to the magnitude of the calculated likelihood value. In another example, the informing function 169 may issue a predetermined sound when the likelihood value exceeds a threshold value.

As explained above, the ultrasound diagnosis apparatus 1 is capable of making the judgment and providing the information about the extent appropriate for the placement of the tool (the catheter). With this arrangement, for example, the operator is able to grasp the timing appropriate for the placement of the tool.

Fourth Embodiment

For example, the ultrasound diagnosis apparatus 1 is further capable of displaying an operation direction of a tool by using a coordinate system that is easy to understand for the operator.

Figure 12:
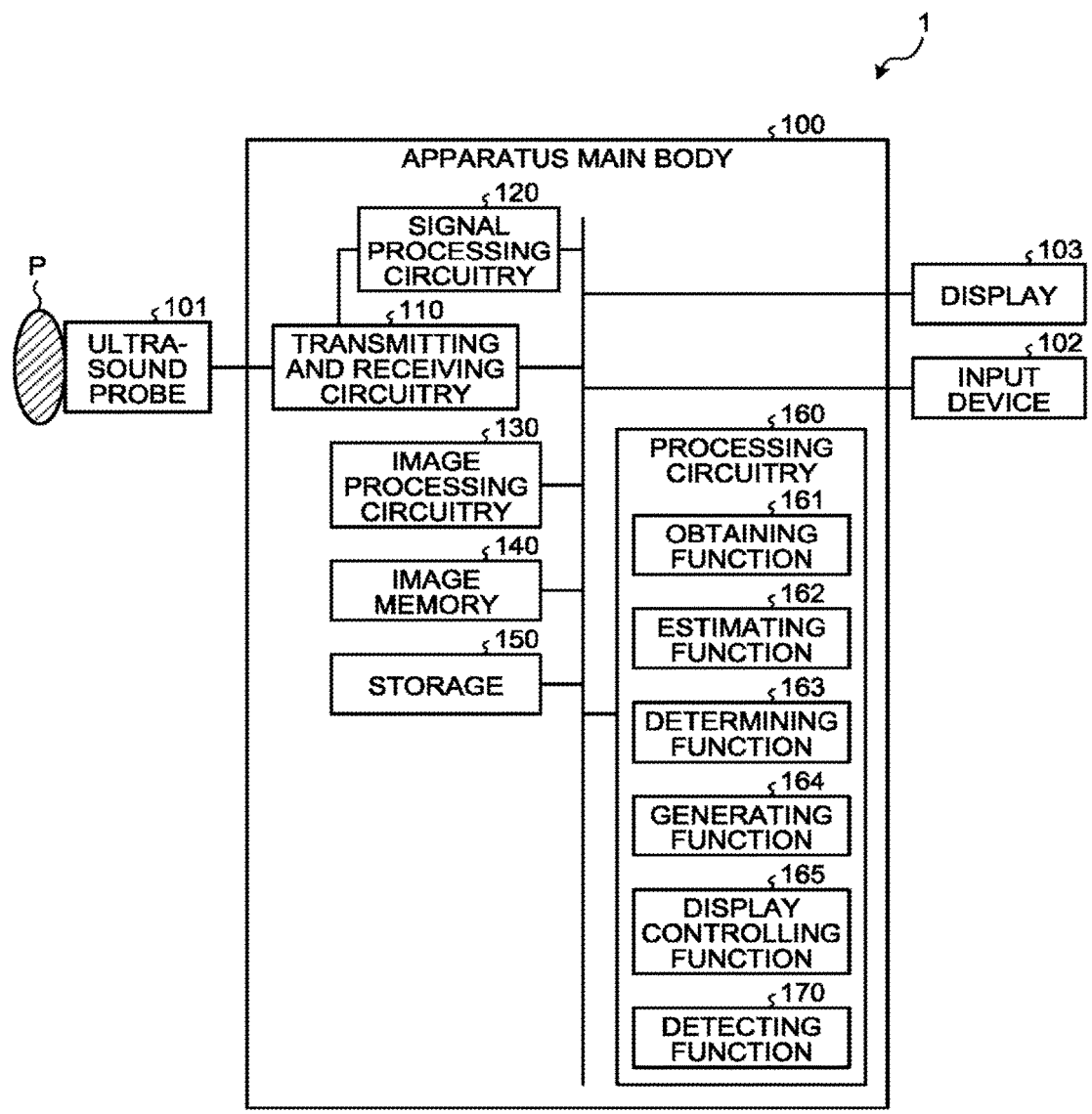
FIG. 12 is a block diagram illustrating an example of an ultrasound diagnosis apparatus according to a fourth embodiment.

FIG. 12 is a block diagram illustrating an example of the ultrasound diagnosis apparatus 1 according to a fourth embodiment. The ultrasound diagnosis apparatus 1 according to the fourth embodiment has a similar configuration to that of the ultrasound diagnosis apparatus 1 illustrated in FIG. 1 and is different in that the processing circuitry 160 further includes a detecting function 170. Thus, as for the fourth embodiment, the explanation will focus on some of the features that are different from those in the first embodiment. The features having the same functions as those explained in the first embodiment will be referred to by using the same reference characters as those in FIG. 1, and the explanations thereof will be omitted.

The detecting function 170 is configured to detect a position within a three-dimensional space of the three-dimensional medical image data. For example, in the fourth embodiment, an acceleration sensor such as a gyro sensor is attached to the ultrasound probe 101 serving as the TEE probe. Before being inserted into the body of the patient P, the acceleration sensor attached to the ultrasound probe 101 registers therein three-dimensional coordinates in a three-dimensional space (e.g., a global coordinate system). For example, the acceleration sensor registers therein the three-dimensional coordinates of the position thereof corresponding to immediately before being inserted into the esophagus of the patient P, i.e., the position of the mouth of the patient P. After that, when the ultrasound probe 101 is inserted into the esophagus of the patient P, the acceleration sensor detects changes in the position caused by the insertion. For example, the detecting function 170 detects three-dimensional coordinates of the current position of the ultrasound probe 101, on the basis of the three-dimensional coordinates registered before the ultrasound probe 101 is inserted into the body of the patient P and the changes in the position detected by the acceleration sensor.

Further, for example, when the ultrasound probe 101 is rendered in an X-ray image taken of the patient P, the detecting function 170 detects the three-dimensional coordinates of the position of the ultrasound probe 101 within the three-dimensional space, on the basis of the X-ray image. More specifically, the detecting function 170 detects the three-dimensional coordinates of the position of the ultrasound probe 101, on the basis of the position of the ultrasound probe 101 in the X-ray image and the positions of the X-ray generator and the X-ray detector used for the imaging of the X-ray image within the three-dimensional space.

In the manner described above, the detecting function 170 detects the three-dimensional coordinates of the position of the ultrasound probe 101 within the three-dimensional space by using the information from at least one selected from between the acceleration sensor and the X-ray image.

Further, the display controlling function 165 causes an operation direction of the tool in the coordinate system of the patient P to be displayed, on the basis of the position within the three-dimensional space detected by the detecting function 170 and the position of the patient P with respect to the three-dimensional space. In this situation, the position of the patient P with respect to the three-dimensional space is obtained from the position of the couch on which the patient P is lying, or the like.

As a result, the display controlling function 165 causes the operation direction of the catheter to be displayed in the coordinate system of the patient P. For example, the display controlling function 165 is able to display the operation direction of the catheter with an expression that uses a site of the body of the patient P as a reference, such as the head side, the leg side, the abdomen side, the back side, the left arm side, or the right arm side of the patient.

First Modification Example of Fourth Embodiment

Further, for example, the ultrasound diagnosis apparatus 1 according to the fourth embodiment may display the operation direction of the tool in a coordinate system of the operator.

For example, the display controlling function 165 causes the operation direction of the tool in the coordinate system of the operator to be displayed, on the basis of the position within the three-dimensional space detected by the detecting function 170 and the position of the operator with respect to the three-dimensional space. In this situation, the position of the operator with respect to the three-dimensional space is obtained by imaging the interior of the room (the interior of the operation room) where the operator is present by using a camera.

With this arrangement, the display controlling function 165 causes the operation direction of the catheter to be displayed in the coordinate system of the operator. For example, the display controlling function 165 is able to display the operation direction of the catheter with an expression such as an upward direction, a downward direction, a right direction, a left direction, or the like as viewed from the operator.

Second Modification Example of Fourth Embodiment

Further, for example, the ultrasound diagnosis apparatus 1 according to the fourth embodiment may display the operation direction of the tool in a coordinate system of an X-ray image.

For example, the display controlling function 165 causes the operation direction of the tool in the coordinate system of the X-ray image to be displayed, on the basis of the position within the three-dimensional space detected by the detecting function 170 and the position of the X-ray image with respect to the three-dimensional space. In this situation, the position of the X-ray image with respect to the three-dimensional space is obtained on the basis of the positions of the X-ray generator and the X-ray detector used for the imaging of the X-ray image within the three-dimensional space.

With this arrangement, the display controlling function 165 causes the operation direction of the catheter to be displayed in the coordinate system of the X-ray image. For example, the display controlling function 165 is able to display the operation direction of the catheter with an expression such as an upward direction, a downward direction, a right direction, a left direction, or the like, in the X-ray image.

Other Embodiments

The present disclosure may be carried out in various different forms other than the embodiments described above.

Display after the Placement of the Tool

For example, in the embodiments above, the display process is explained up to the time when the clip part 11 of the catheter is placed with the mitral valve; however, it is also possible to control the display process performed after the placement.

For example, when the tool has been placed, the display controlling function 165 may cause a cross-sectional image including the tool to be displayed. For example, the display controlling function 165 detects that the tool has been placed. More specifically, the display controlling function 165 detects that the clip part 11 has been placed when the clip part 11 and the tubular part 12 of the catheter has become distant from each other in the binarized image 20 described above. After that, when detecting that the clip part 11 has been placed, the display controlling function 165 generates and displays the cross-sectional images 40 and 41 taken along the advancing direction of the catheter observed immediately before the placement.

As explained above, the ultrasound diagnosis apparatus 1 is capable of displaying the cross-sectional images including the tool, even after the tool has been placed.

The constituent elements of the apparatuses illustrated in the drawings are based on functional concepts. Thus, it is not necessary to physically configure the constituent elements as indicated in the drawings. In other words, the specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a computer program analyzed and executed by the CPU or may be realized as hardware using wired logic.

With regard to the processes explained in the embodiments and modification examples described above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, various information including various types of data and parameters that are presented in the above text and the drawings.

It is possible to realize any of the ultrasound imaging methods explained in the embodiments and the modification examples above, by causing a computer such as a personal computer or a workstation to execute an ultrasound imaging computer program (hereinafter, "ultrasound imaging program") prepared in advance. It is possible to distribute the ultrasound imaging method via a network such as the Internet. Further, the ultrasound imaging method may be implemented as being recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like and being read from the recording medium by a computer.

According to at least one aspect of the embodiments described above, it is possible to generate the display image in which it is possible to view the position and the advancing direction of the tool with respect to the heart valve.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
processing circuitry configured to:
obtain three-dimensional medical image data, taken by using an ultrasound probe, of a region including a heart valve of a patient and a catheter inserted into a heart chamber of the patient;
determine an advancing direction of a tip end part of the catheter by obtaining information on a position and a posture of the tip end part included in the three-dimensional medical image data, by using at least one of shape information indicating a shape of the tip end part and reflection characteristic information indicating ultrasound reflection characteristics of the tip end pan;
set a point of view based on the position of the tip end part;
set a line of sight based on the advancing direction of the tip end part;
generate a display image corresponding to the set point of view and the set line of sight from the three-dimensional medical image data; and
cause the display image to be displayed.

2. The ultrasound diagnosis apparatus according to claim 1, wherein the processing circuitry is configured to obtains the information on the position and the posture of the tip end part, which includes one of a clip part and an artificial valve to be placed with a mitral valve.

3. The ultrasound diagnosis apparatus according to claim 1, wherein the display image caused to be displayed by the processing circuitry is an image expressing the three-dimensional medical image data in a three-dimensional manner.

4. The ultrasound diagnosis apparatus according to claim 3, wherein the display image caused to be displayed by the processing circuitry is of a volume rendering image and a surface rendering image.

5. The ultrasound diagnosis apparatus according to claim 1, wherein the processing circuitry is further configured to generate, as the display image, a cross-sectional image taken along the advancing direction of the tip end part.

6. The ultrasound diagnosis apparatus according to claim 1, wherein the processing circuitry is further configured to estimate a position and a posture in and with which the catheter should be installed with respect to a position and a posture of the heart valve.

7. The ultrasound diagnosis apparatus according to claim 6, wherein the processing circuitry is further configured to cause an image to be displayed simultaneously with the display image, the image indicating a direction in which the position and the posture of the catheter move toward and away from the estimated position and posture of the catheter to be installed.

8. The ultrasound diagnosis apparatus according to claim 1, wherein the processing circuitry is further configured to:
determine a moving direction of the catheter based on positions of the catheter at mutually-different times; and
cause an image indicating the determined moving direction of the catheter to be displayed simultaneously with the display image.

9. The ultrasound diagnosis apparatus according to claim 1, wherein the processing circuitry is further configured to cause an X-ray image generated based on X-rays that have passed through the patient, to be displayed simultaneously with the display image.

10. The ultrasound diagnosis apparatus according to claim 9, wherein the processing circuitry is further configured to:
detect a position within a three-dimensional space of the three-dimensional medical image data; and
cause an operation direction of the catheter in a coordinate system of the X-ray image to be displayed, based on the detected position within the three-dimensional space and a position of the X-ray image with respect to the three-dimensional space.

11. The ultrasound diagnosis apparatus according to claim 1, wherein the processing circuitry is further configured to
obtain a locus of a movement up to a time when the catheter is installed with the heart valve of the patient, from a result of a pre-surgical-operation simulation performed on the patient, and
cause an image for guiding an advancing course of the catheter to be displayed, by aligning a position of the locus of the movement with a position of the three-dimensional medical image data.

12. The ultrasound diagnosis apparatus according to claim 1, wherein the processing circuitry is further configured to:
judge a degree of appropriateness of a placing position of the tip end part based on a model of movements of the heart valve obtained by performing a pre-surgical-operation simulation on the patient; and
provide information about a result of the judgment.

13. The ultrasound diagnosis apparatus according to claim 1, wherein the processing circuitry is further configured to:
detect a position within a three-dimensional space of the three-dimensional medical image data; and
cause an operation direction of the catheter in a coordinate system of the patient to be displayed, based on the detected position within the three-dimensional space and a position of the patient with respect to the three-dimensional space.

14. The ultrasound diagnosis apparatus according to claim 1, wherein the processing circuitry is further configured to:
   detect a position within a three-dimensional space of the three-dimensional medical image data; and
   cause an operation direction of the catheter in a coordinate system of an operator to be displayed, based on the detected position within the three-dimensional space and a position of the operator with respect to the three-dimensional space.

15. The ultrasound diagnosis apparatus according to claim 1, wherein, in accordance with an instruction from an operator, the processing circuitry is further configured to generate one of a volume rendering image that uses the tip end part as a point of view and a volume rendering image that uses a position behind the tip end part as a point of view.

16. The ultrasound diagnosis apparatus according to claim 1, wherein the three-dimensional medical image data obtained by the processing circuitry is data taken by a transesophageal echocardiography probe that is the ultrasound probe.

17. The ultrasound diagnosis apparatus according to claim 1, wherein the processing circuitry is further configured to cause a cross-sectional image including the tip end part to be displayed when the tip end part has been placed.

18. An image processing method, comprising:
   obtaining three-dimensional medical image data, taken by using an ultrasound probe, of a region including a heart valve of a patient and a catheter inserted into a heart chamber of the patient;
   determining an advancing direction of a tip end part of the catheter by obtaining information on a position and a posture of the tip end part included in the three-dimensional medical image data, by using at least one of shape information indicating a shape of the tip end part and reflection characteristic information indicating ultrasound reflection characteristics of the tip end part;
   setting a point of view based on the position of the tip end part;
   setting a line of sight based on the advancing direction of the tip end part;
   generating a display image corresponding to the set point of view and the set line of sight from the three-dimensional medical image data; and
   causing the display image to be displayed.

19. The image processing method of claim 18, wherein the setting steps are performed automatically without human intervention.

* * * * *